US007105666B2

(12) United States Patent
Hammarström et al.

(10) Patent No.: US 7,105,666 B2
(45) Date of Patent: Sep. 12, 2006

(54) SYNTHESIS OF PURINE DERIVATIVES

(75) Inventors: Lars G.J. Hammarström, Stockholm (SE); Nancy Elisabth Krauss, Mountain View, CA (US); Sharada Shenvi Labadie, Sunnyvale, CA (US); David Bernard Smith, San Mateo, CA (US); Francisco Xavier Talamas, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 190 days.

(21) Appl. No.: 10/608,657

(22) Filed: Jun. 27, 2003

(65) Prior Publication Data

US 2004/0034224 A1 Feb. 19, 2004

Related U.S. Application Data

(60) Provisional application No. 60/392,081, filed on Jun. 27, 2002.

(51) Int. Cl.
*C07D 473/16* (2006.01)
*C07D 473/34* (2006.01)
*C07D 473/18* (2006.01)
*C07D 473/24* (2006.01)
*C07D 239/50* (2006.01)

(52) U.S. Cl. ................. 544/276; 544/277; 544/317
(58) Field of Classification Search ............. 544/276, 544/277
See application file for complete search history.

(56) References Cited

U.S. PATENT DOCUMENTS 3,930,005 A * 12/1975 Wojnar et al. ......... 514/263.37
2004/0192912 A1 * 9/2004 Pendri et al. ............... 544/276

FOREIGN PATENT DOCUMENTS

EP 0 084 758 8/1983

OTHER PUBLICATIONS

Brown, Australian Journal of Chemistry 38(3) 467-474 (1985).*
B. R. Baker, et al J. Organic Chemistry 19 (1954) pp. 631-637.*
John W. Daly J. Organic CHem 21 (1956) pp. 177-179.*
Buckman, et al.; "Design, Synthesis, and Biological Activity of Novel Purine and Bicyclic Pyrimidine Factor Xa Inhibitors," Bioorganic & Medicinal Chemistry Letters; (1998) pp. 2235-2240; vol. 8.
Miyabe, et al., "Samarium Diiodide-induced Radical Cyclization of Oxime Ether Connected with Formyl Group," Tetrahedron, vol. 54, (2000) pp. 5077-5083.
Jeffery, et al., "Synthesis of Acyclic Nucleoside and Nucleotide Analogues from Amino Acids: A Convenient Approach to a PMEA-PMPA Hybrid," Tetrahedron, vol. 56, (2000) pp. 5077-5083.
Gauvry, et al., "Novel Preparation of *cis,cis*-Trisubstituted Cyclopropane Nucloesides," Tetrahedron, vol. 55 (1999) pp. 1321-1328.
Csuk, et al., "Enantiomerically Pure Cyclopropanoid Nucleoside Analogues: Synthesis and Analysis," Tetrahedron, vol. 52:18, (1996) pp. 6383-6396.
Guillier, et al., "Solid-Phase Synthesis of 2,4,6-Triaminopyrimidines," Chem. Eur. J., vol. 5:12, (1999) pp. 3450-3458.
Dorff, et al., "Novel solid-base preparation of 2,6,9-trisubstituted purines for combinatorial library generation," Tetrahedron Letters, vol. 42, (2001) pp. 2771-2773.
Ding, et al., "A Concise and Traceless Linker Strategy toward Combinatorial Libraries of 2,6,9-Substituted Purines," J. Org. Chem., vol. 66, (2001) pp. 8273-8276.
Di Lucrezia, et al., "Solid Phase Synthesis of Purines from Pyrimidines," J. Comb. Chem. vol. 2, (2000) pp. 249-253.
Sheng Ding et al., Resin-Capture and Release Strategy toward Combinatorial Libraries of 2,3,9-substitued purines, J. Comb. Chem., 2002, 4, 183.

* cited by examiner

*Primary Examiner*—Mark L. Berch
(74) *Attorney, Agent, or Firm*—Grant D. Green

(57) ABSTRACT

The present invention provides a method for producing 2-, 6-, 8- and 9-substituted purine compounds from 4,6-dihalo-5-nitro-2-alkyl-pyrimidine compounds in solution or by solid phase techniques. The present process provides for the sequential introduction of amine substituents at the 4- and 6-positions, displacement of an alkylsulfony group at the 2-position of the pyrimidine, reduction of the nitro group and formation of the imidazole portion of the purine compound. Furthermore, the methods of the present invention are ideally suited to the preparation of a library of purine compounds.

9 Claims, No Drawings

US 7,105,666 B2

SYNTHESIS OF PURINE DERIVATIVES

CROSS REFERENCE TO RELATED INVENTION

This application claims the priority benefit under Title 35 U.S.C. 119(e) of U.S. Provisional Application 60/392,081, filed Jun. 27, 2002, the disclosure of which is herein incorporated by reference in its entirety.

FIELD OF THE INVENTION

The present invention relates to a method for producing highly substituted purine compounds, and to a combinatorial library of purine compounds.

BACKGROUND OF THE INVENTION

Purine compounds have a wide variety of pharmacological activities. For example, many purine compounds are kinase inhibitors. Therefore, a number of solution and solid-phase methods for synthesizing purine compounds have been recently advanced.

Conventional methods for synthesizing purine compounds generally involve displacing a leaving group in a preformed purine ring system with a desired nucleophile or producing the purine ring system from an appropriately substituted pyrimidine ring system. However, none of the methods currently available provides synthesis of highly substituted purine compounds, e.g., purines having substituents on the 2-, 6-, 8-, and 9-positions with the ability to vary the substituent on each position.

Synthesis of purines from a pyrimidine compound often requires reduction of a nitro group that is present in the pyrimidine ring system. Unfortunately, currently known reduction methods give only partial reduction, are not consistently reproducible, or yield a product that is contaminated with undesirable inorganic salts which are difficult to remove. See *J. Comb. Chem.*, 2000, 2, 249–253.

Therefore, there is a need for a method for synthesis of a highly substituted purine compounds. There is also a need for a method for selectively reducing a nitro substituent on a pyrimidine ring on a solid support-bound pyrimidine compound which provides a solid support-bound amino pyrimidine compound that is substantially free of inorganic salts.

SUMMARY OF THE INVENTION

The present invention provides a substituted purine compound, a combinatorial library of purine compounds, and a method for producing a substituted purine and a library of purine compounds. In particular, the present invention provides a method for producing a purine compound from a pyrimidine compound.

One aspect of the present invention provides a method for producing a substituted purine compound of the formula:

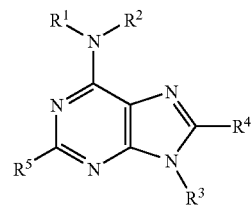

wherein
  $R^1$ is a solid support, hydrogen, alkyl, cycloalkyl, or aryl;
  $R^2$ is alkyl, cycloalkyl, aryl, or a nitrogen protecting group;
  $R^3$ is hydrogen, alkyl, cycloalkyl, aryl, or a nitrogen protecting group;
  $R^4$ is hydrogen, alkyl, aryl, or —$NR^6R^7$, where each of $R^6$ and $R^7$ is independently hydrogen, alkyl, aryl, or cycloalkyl; and
  $R^5$ is alkyl, alkoxy, alkenyl, alkynyl, aryl, aryloxy, cycloalkyl, cycloalkoxy, alkylthio, arylthio, or —$NR^8R^9$, where each of $R^8$ and $R^9$ is independently hydrogen, alkyl, cycloalkyl, aryl, or a nitrogen protecting group, or $R^8$ and $R^9$ together with the nitrogen atom to which they are attached to form a heterocyclyl ring;

said method comprising:
  (a) contacting a 5-nitropyrimidine compound of the formula:

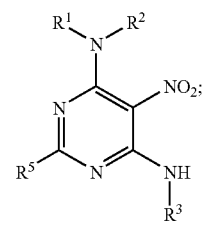

with a reducing agent to produce a 4, 5, 6-triaminopyrimidine of the formula:

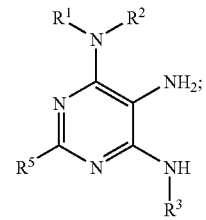

and
  (b) forming a purine ring by contacting the 4, 5, 6-triaminopyrimidine with a cyclizing agent to produce the substituted purine.

Preferably, methods of the present invention comprise producing a solid support-bound purine compound, i.e., where $R^1$ is a solid support. Most conventional methods for reducing the nitro group on a solid support-bound pyrimidine lead to cleavage of the pyrimidine from the solid support or contamination of the product with inorganic salts or incomplete reduction. In contrast, the present invention provides methods for reducing a nitro-substituted solid support-bound pyrimidine compound without cleaving a significant amount of the pyrimidine from the solid-support. Thus, substantially all of the solid support-bound pyrimidine ring remain bound to the solid support during the nitro group reducing process.

Moreover, the reduction products of the present invention are substantially free of inorganic salts.

Preferably, the nitro group reducing agent is selected from the group consisting of:

(a) $CrX_2$, wherein each X is independently halide, and (b) a mixture of 1,1'-dialkyl-4,4'-bipyridinium dihalide and a thiosulfate compound.

In one embodiment, the nitro reducing step comprises the presence of a protic solvent.

In another embodiment, the solid support-bound purine is cleaved from the solid support to produce the purine compound where $R^1$ is hydrogen. $R^1$ group can be further modified by any conventional process known to one skilled in the art, for example, by alkylation, acylation, and the like.

Preferably, the cyclizing agent is an orthoester, an acyl anhydride, an acyl halide, a mixture of an isothiocyanate and an oxidizing agent, a mixture of an isocyanate and an oxidizing agent, or a mixture of an aldehyde and an oxidizing agent.

In one embodiment, the 5-nitropyrimidine compound is produced by steps comprising:

(a) contacting a 4,6-dihalo-5-nitro-2-thioether pyrimidine of the formula:

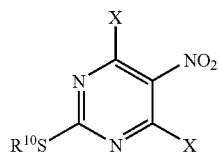

with a first amine compound of the formula $Z^1H$ to produce a 6-aminopyrimidine of the formula:

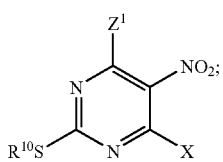

(b) contacting the 6-aminopyrimidine with a second amine compound of the formula $Z^2H$ to produce a 4,6-diaminopyrimidine of the formula:

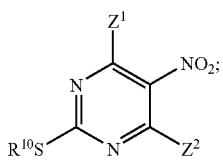

(c) contacting the 4,6-diaminopyrimidine with an oxidizing agent to produce a 2-sulfonylpyrimidine of the formula:

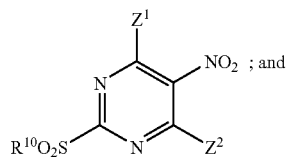

(d) contacting the 2-sulfonylpyrimidine with a nucleophile of the formula $R^5$—M to produce the 5-nitropyrimidine compound, wherein one of $Z^1$ and $Z^2$ is —$NR^1R^2$ and the other is —$NHR^3$;

$R^1$, $R^2$, $R^3$, and $R^5$ are those defined herein;

$R^{10}$ is alkyl, cycloalkyl, or aryl;

M is hydrogen, metal, or a metal complex; and each X is independently halide.

Another aspect of the present invention provides a method for producing a substituted purine of the formula:

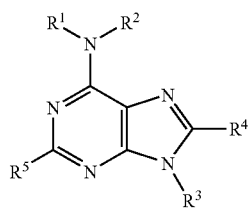

said method comprising:

(a) contacting a 4,6-dihalo-5-nitro-2-thioether pyrimidine of the formula:

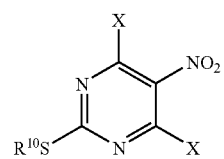

with a first amine compound of the formula $Z^1H$ to produce a 6-aminopyrimidine of the formula:

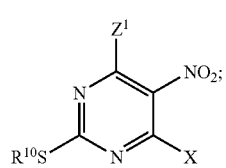

(b) contacting the 6-aminopyrimidine with a second amine compound of the formula $Z^2H$ to produce a 4,6-diaminopyrimidine of the formula:

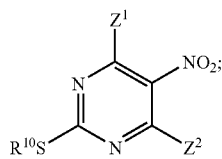

(c) contacting the 4,6-diaminopyrimidine with an oxidizing agent to produce a 2-sulfonylpyrimidine of the formula:

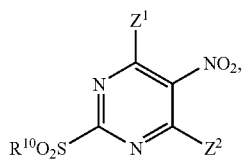

wherein one of $Z^1$ and $Z^2$ is —$NR^1R^2$ and the other is —$NHR^3$;

(d) contacting the 2-sulfonylpyrimidine with a nucleophilic compound of the formula $R^5$—M to produce a 5-nitropyrimidine of the formula:

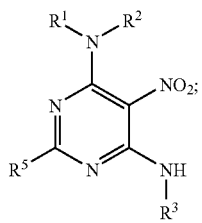

(e) contacting the 5-nitropyrimidine with a reducing agent to produce a 4,5,6-triaminopyrimidine of the formula:

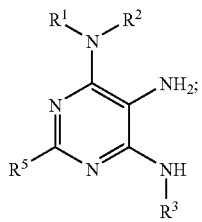

and (f) contacting the 4,5,6-triaminopyrimidine with a cyclizing agent to produce the substituted purines, wherein $R^1$, $R^2$, $R^3$, $R^5$, and M are those defined herein.

Methods of the present invention are particularly useful in producing a combinatorial library of substituted purine compounds. Such a library of compounds can be produced on a solid support, e.g., where $R^1$ is a solid support. Each purine compound in the combinatorial library can be spatially separated or the library can comprises a mixture of different purine compounds.

In one embodiment, the combinatorial library is formed on a plurality of particles (i.e., solid support), each particle having a surface coating of purine molecules of the same substituents.

In another embodiment, the purine compounds are cleaved from the solid support to produce a library of free, i.e., non-solid support-bound, substituted purine compounds.

Yet another aspect of the present invention provides a combinatorial library of purines, wherein each purine in the library is of the formula:

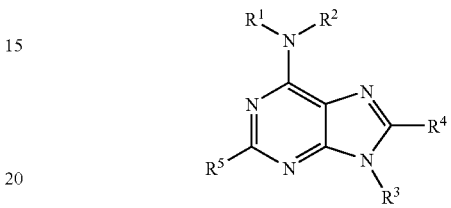

wherein $R^1$, $R^2$, $R^3$, $R^4$, and $R^5$ are those defined herein.

Yet still another aspect of the present invention provides a method for reducing a nitro substituent on a pyrimidine ring which is covalently attached to a solid support, wherein the pyrimidine ring is optionally substituted with one, two, or three independent non-hydrogen substituents, said method comprising:

(a) reducing the nitro functional group to an amino functional group by contacting the solid support-bound pyrimidine compound with chromium dihalide to produce a reaction mixture comprising a solid support-bound amino pyrimidine compound; and (b) removing the solid support-bound amino pyrimidine compound from the reaction mixture, wherein the solid support-bound amino pyrimidine compound that is removed from the reaction mixture is substantially free of inorganic salts.

In one embodiment, substantially all of the solid support-bound pyrimidine ring remains covalently bound to the solid support during the nitro group reducing step.

Preferably, the reaction mixture for reducing the nitro group comprises a protic solvent.

In another embodiment, the chromium dihalide is chromium dichloride.

DETAILED DESCRIPTION OF THE INVENTION.

I. Definitions

Unless otherwise stated, the terms below have the following meanings:

A "2,6,8,9-substituted purine" refers to a purine compound which is produced using a method of the present invention. Depending on the particular reagent used in each step of the process, the substituent(s) on the purine ring can be hydrogen. While hydrogen is not considered to be a "substituent" in a conventional sense, the present invention includes "hydrogen" as being a substituent.

"Alkyl" refers to aliphatic hydrocarbons which can be straight or branched chain groups. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur, substituted or unsubstituted nitrogen atoms, and the like.

"Alkoxy" refers to a moiety —OR$^a$, where R$^a$ is alkyl group as defined herein.

"Alkenyl" refers to aliphatic hydrocarbons which can be straight or branched chain groups having at least one carbon-carbon double bond with the understanding that the point of attachment of an alkenyl group is through one of the carbon atom of the carbon-carbon double bond. Alkenyl groups optionally can be substituted with one or more substituents, such as a halogen, alkyl, alkenyl, alkynyl, aryl, hydroxy, amino, thio, alkoxy, carboxy, oxo or cycloalkyl. There may be optionally inserted along the alkenyl group one or more oxygen, sulfur, substituted or unsubstituted nitrogen atoms, and the like.

"Alkynyl" refers to aliphatic hydrocarbons which can be straight or branched chain groups having at least one carbon-carbon triple bond with the understanding that the point of attachment of an alkynyl group is through one of the carbon atom of the carbon-carbon triple bond. Alkynyl groups optionally can be substituted with one or more substituents, such as a halogen, alkyl, alkenyl, alkynyl, aryl, hydroxy, amino, thio, alkoxy, carboxy, oxo or cycloalkyl. There may be optionally inserted along the alkynyl group one or more oxygen, sulfur, substituted or unsubstituted nitrogen atoms, and the like.

"Aryl" refers to aromatic ring moieties including carboaryls, such as mono- and bicyclic aromatic carbocyclic ring moieties; and heteroaryls, such as mono- and bicyclic aromatic heterocyclic ring moieties. Aryl groups can be substituted with one or more substituents, such as a halogen, alkyl, alkenyl, alkynyl, aryl, hydroxy, amino, thio, cycloalkyl, and the like.

"Aryloxy" refers to a moiety —OR$^b$, where R$^b$ is aryl group as defined herein.

"Combinatorial library of purines" refers to a library comprising a plurality of purine compounds, typically at least 20 different purine compounds. The combinatorial library can be prepared by any conventional combinatorial synthetic methods known to one skilled in the art, for example, parallel synthetic methods, split-pool synthetic methods, and combinations thereof. Therefore, the term "combinatorial library of purines" refers to a library comprising a mixture of purine compounds as well as a plurality of different purine compounds in which each different purine compound is spatially separated, e.g., contained in a separate vessel.

"Cyclizing agent" refers to a reagent which forms a purine ring moiety from a diamino pyrimidine compound. Preferably, cyclizing agent is an orthoester, an acyl anhydride, an acyl halide, a mixture of an isothiocyanate and an oxidizing agent, a mixture of an isocyanate and an oxidizing agent, or a mixture of an aldehyde and an oxidizing agent.

"Cycloalkyl" refers to alicyclic hydrocarbons including carbocycles, such as mono- and bicyclic non-aromatic carbocyclic ring moieties; and heterocycles, such as mono- and bicyclic non-aromatic heterocyclic ring moieties. Cycloalkyl groups can be substituted with one or more substituents, such as halogen, alkyl, alkenyl, alkynyl, aryl, hydroxy, amino, thio, alkoxy, carboxy, oxo, cycloalkyl, and the like.

"Cylcoalkoxy" refers to a moiety —OR$^c$, where R$^c$ is cycloalkyl group as defined herein.

"Different purine compounds" refers to purine compounds having different substituents, different substituent patterns, or combinations thereof within the purine ring. Thus, purines with the same substituent groups but different position of these substituents within the purine ring, i.e., regioisomers, constitute different compounds. Further, purines with the same substituents, but with differing stereochemistry within the substituent, i.e., stereoisomers, also constitute different compounds.

"Halide" means halogen, which includes F, Cl, Br, and I.

"Heterocyclyl" means a non-aromatic cyclic moiety of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group, with the understanding that the point of attachment of heterocyclyl is through the hetereoatom. The heterocyclyl ring may be optionally substituted independently with one, two, or three substituents selected from halogen, alkyl, alkenyl, alkynyl, aryl, hydroxy, amino, thio, alkoxy, carboxy, oxo, cycloalkyl, and the like. More specifically the term heterocyclo includes, but is not limited to, piperidino, piperazino, morpholino and thiomorpholino, thiomorpholino-1-oxide, thiomorpholino-1,1-dioxide, and the like.

"Leaving group" has the meaning conventionally associated with it in synthetic organic chemistry, i.e., an atom or a group capable of being displaced by a nucleophile and includes halo (such as chloro, bromo, and iodo), alkylsulfonyl, arylsulfonyl, alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Nitrogen protecting group" refers to a moiety, except alkyl groups, that when attached to a nitrogen atom in a molecule masks, reduces or prevents reactivity of the nitrogen atom. Examples of nitrogen protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996), which are incorporated herein by reference in their entirety. Representative nitrogen atom protecting groups include formyl, acetyl, trifluoroacetyl, benzyl, benzyloxycarbonyl (CBZ), tert-butoxycarbonyl (Boc), trityl, substituted trityl groups, allyloxycarbonyl, 9-fluorenylmethyloxycarbonyl (FMOC), nitro-veratryloxycarbonyl (NVOC), optionally substituted benzyl, and allyl groups, and the like.

The materials upon which the combinatorial syntheses of the invention are performed are referred, interchangeably, to as solid supports, beads, and resins. These terms are intended to include:

a) beads, pellets, disks, fibers, gels, surfaces, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface;

b) soluble supports such as low molecular weight non-cross-linked polystyrene; and c) derivatized forms thereof.

"Solid support-bound compound" means that the compound is covalently attached to a solid support.

"Substantially free of inorganic salt" means that the inorganic salt is present in an amount of about 10 mole percent or less, preferably about 5 mole percent or less, more preferably about 1 mole percent or less, and most preferably about 0.1% mole percent or less of the desired product.

"alkylthio" refers to a moiety of the formula $-SR^d$, where $R^d$ is alkyl as defined herein.

"arylthio" refers to a moiety of the formula $-SR^e$, where $R^e$ is aryl as defined herein.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

II. Introduction

Unless otherwise stated, the following numbering system is used to describe positions on the purine ring.

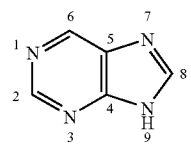

In one aspect, the present invention is based on the discovery by the present inventors of a synthesis of highly substituted purine compounds. In particular, present inventors have discovered selective reaction conditions that allow introduction of desired substituents on the 2-, 6-, 8- and 9-positions of a purine compound. As such, methods of the present invention are particularly useful in synthesis of a highly substituted purine compounds and/or a combinatorial library of purine compounds.

III. Synthesis of Purine Compounds

Methods of the present invention are applicable to a solution phase and a solid phase synthesis of purine compounds. In one aspect, methods of the present invention comprise producing a purine compound, preferably a highly substituted purine compound, by reacting an appropriately substituted pyrimidine compound with an appropriately substituted cyclizing compound. In particular, methods of the present invention allow introduction of each substituent on the purine ring system; therefore, a highly substituted purine compound can be readily produced.

In one specific embodiment, the present invention provides a method for producing a purine compound of the formula:

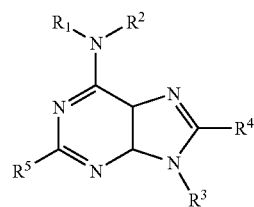

where
$R^1$ is a solid support, hydrogen, alkyl, cycloalkyl, or aryl;
$R^2$ is alkyl cycloalkyl, aryl, or a nitrogen protecting group;
$R^3$ is hydrogen, alkyl, cycloalkyl, aryl, or a nitrogen protecting group;
$R^4$ is hydrogen, alkyl, aryl, or $-NR^6R^7$, where each of $R^6$ and $R^7$ is independently hydrogen, alkyl, aryl, or cycloalkyl; and
$R^5$ is alkyl, alkoxy, alkenyl, alkynyl, aryl, aryloxy, cycloalkyl, cycloalkoxy, alkylthio, arylthio, or $-NR^8R^9$, where each of $R^8$ and $R^9$ is independently hydrogen, alkyl, cycloalkyl, aryl, or a nitrogen protecting group, or $R^8$ and $R^9$ together with the nitrogen atom to which they are attached to form a heterocyclyl.

Preferably, $R^1$ is a solid support.
Preferably, $R^4$ is hydrogen or alkyl.
Preferably, $R^5$ is $-NR^8R^9$, where $R^8$ and $R^9$ are those defined herein.
Preferably, each of $R^6$ and $R^7$ is independently hydrogen or alkyl.
Yet in another embodiment, $R^3$ is hydrogen, alkyl, or cycloalkyl.

Still further, combinations of the preferred groups or a particular embodiment described above form other preferred or specific embodiments. For example, in one group of a particularly preferred embodiment $R^1$ is a solid support, $R^3$ is hydrogen or alkyl, $R^4$ is hydrogen or alkyl, and $R^5$ is $-NR^8R^9$.

In one particular aspect, the present invention provides a method for producing a purine compound of Formula I by reacting a 4, 5, 6-triamino pyrimidine compound of the formula:

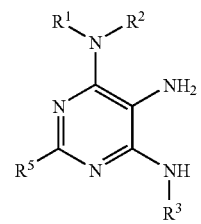

where $R^1$, $R^2$, $R^3$, and $R^5$ are those defined herein, with a cyclizing compound to produce purine ring system of compound of Formula I. Exemplary cyclizing agents include aldehydes, orthoesters, activated carboxylic acids, isocyanates, and isothiocyanates. Exemplary activated carbonyl compounds include acyl halides, anhydrides, and other activated carbonyl compounds known to one skilled in the art.

As shown in Scheme I below, the substituents on the 2-, 6-, and 9-positions of purine of Formula I are derived from the pyrimidine compound, whereas the substituent on the 8-position is derived from the cyclizing compound.

Scheme I

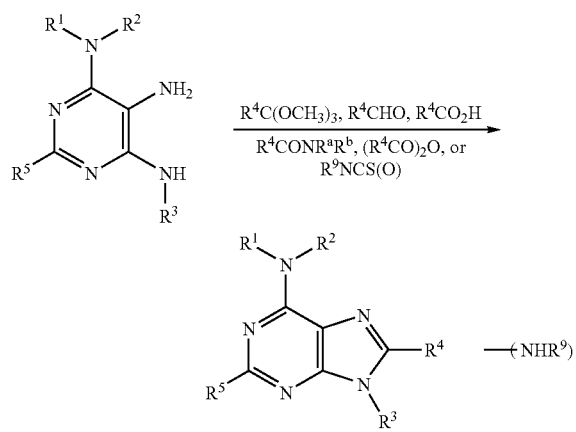

Thus, when an isocyanate or a thioisocyanate is used as the cyclizing agent, the resulting substituent on the 8-position is an amino moiety, i.e., —NHR$^9$. When an activated carboxylic acid, an orthoester, an amide, or an aldehyde is used as the cyclizing agent, the resulting substituent on the 8-position is R$^4$ as shown in Scheme I.

In some instances, the presence of an oxidizing agent facilitates or is required for the formation of a purine ring system. Typically, the oxidizing agent is a mild oxidizing agent which is conventionally known in synthesis of an aromatic ring system. Exemplary oxidizing agents include carbodiimides, such as DCC and diisopropylcarbodiimide; quinones, such as DDQ; and air. When an isothiocyanate is used as the cyclizing agent, typically a carbodiimide, preferably diisopropylcarbodiimde, is used as an oxidizing agent. And when an aldehyde is used as the cyclizing compound, a quinone, preferably DDQ, is used as an oxidizing agent.

When an orthoester is used as a cyclizing agent, it has been found that some reaction conditions result in formation of non-cyclic intermediate where the 5-position amino group is substituted with —C(═O)—R$^4$ group. By increasing the reaction temperature and/or the reaction time one can convert the non-cyclic intermediate to a purine compound. Alternatively, exposure of the non-cyclic intermediate to oxidizing conditions, e.g., exposure to air, also leads to formation of the purine ring.

It should be appreciated that when R$^1$ is hydrogen and R$^2$ is a different moiety than R$^3$, potentially two different purines can be formed. To avoid formation of two regioisomeric purines, methods of the present invention, preferably, comprise using a pyrimidine of Formula II where the reactivity of the amino group on the 6-position (i.e., —NR$^1$R$^2$, where R$^1$ is hydrogen) is preferably slower than the reactivity of the amino group on the 4-position (i.e., —NHR$^3$) of the pyrimidine ring. Such a difference in reactivity can be achieved by having different substituents on the nitrogen atom of the amino groups. Typically, the amino group on the 6-position, i.e., —NR$^1$R$^2$, is a tertiary amine, and the amino group on the 4-position, i.e.,—NHR$^3$, is a secondary or primary amino group. Because the purine ring system is symmetrical, the position substituted with the —NR$^1$R$^2$ group is arbitrarily designated as the 6-position and the position substituted with the —NHR$^3$ group is arbitrarily designated as the 4-position.

Synthesis of Pyrimidine of Formula II

As shown in Scheme I above, three of the four substituents on the purine ring are derived from substituents on pyrimidine of Formula II. Thus, another aspect of the present invention provides a method for producing 4,5,6-triamino pyrimidine compound of Formula II. In one particular embodiment, the 4, 5, 6-triamino pyrimidine compound of Formula II is produced from a corresponding 5-nitro-4,6-diamino pyrimidine of Formula:

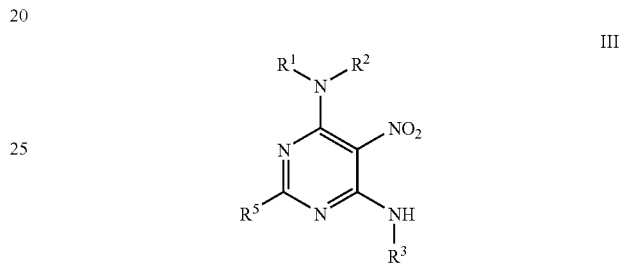

III where R$^1$, R$^2$, R$^3$, and R$^5$ are those defined herein. The method generally comprises selective reduction of the nitro group. When 5-nitro-4,6-diamino pyrimidine of Formula III is attached to a solid support many conventional nitro group reduction conditions result in cleavage of the pyrimidine moiety from the solid support. Other conventional reducing agents lead to an inconsistent result or a product that is contaminated with undesirable inorganic salts. See, for example, Di Lucrezia et al., *J. Comb. Chem.*, 2000, 2, 249–253.

The present inventors have discovered that the nitro group of a solid support-bound pyrimidine can be cleanly reduced to an amino group using a chromium dihalide compound, i.e., CrX$_2$, where X is a halide. A particularly preferred chromium dihalide compound is chromium dichloride. It has been found that reduction of nitro group of a solid support-bound pyrimidine with a chromium dihalide compound produces a solid support-bound amino pyrimidine which is substantially free of inorganic salts. In addition, using a chromium dihalide as the reducing agent results in substantially all pyrimidine ring being remain bound to the solid support. Typically, at least about 75% of the pyrimidine ring remain bound to the solid support after the reducing step. Preferably, at least about 90%, and more preferably at least about 99% of the pyrimidine ring remains bound to the solid support after the reducing step.

In some cases, the reduction of solid support-bound nitro pyrimidine compound of Formula III is facilitated by the presence of a protic solvent. Suitable protic solvents include water and alcohols, e.g., methanol, ethanol, and isopropanol.

Typical conditions for reducing the nitro moiety in nitro pyrimidine of Formula III include adding a reducing agent to a reaction mixture comprising the solid support-bound nitro pyrimidine of Formula II in a mixture of inert organic solvent. As stated above, in some instances the reaction mixture preferably includes a protic solvent, which has shown to facilitate reduction of the nitro group. Thus, the reduction of nitro group is generally achieved using a solvent mixture comprising a relatively inert organic solvent, such as DMF, dichloromethane, or THF; and a protic solvent, such as water or an alcohol.

In theory, the reduction of a nitro group requires 6 stoichiometric equivalents (i.e., one functional equivalent) of the reducing agent. Generally, however, an excess amount of reducing agent is added to ensure a relatively fast reduction and/or to increase the yield. Typically from about 10 stoichiometric eq. to about 16 stoichiometric eq. of the reducing agent is used.

Alternatively, a catalytic amount of chromium chloride can be used by adding manganese (Mn) and TMS-Cl or other suitable proton surrogate. In particular, a solid Mn can be used in this embodiment thereby allowing a facile product isolation process.

Other suitable reducing agents include a mixture of ammonium halide and iron, and a mixture of quaternary pyridinium halide (e.g., 1,1'-dioctyl-4,4'-bipyridinium dibromide) and a metal thiosulfate (e.g., $Na_2S_2O_3$) in dichloromethane/water mixture, preferably in THF/water mixture.

Synthesis of Nitro Pyrimidine of Formula III

Again referring to Scheme I, the substituents on the 2-, 6-, and 9-position of the purine ring system is determined by the corresponding substituents on the pyrimidine ring system. Since the second ring system is formed from the amino groups on the 4- and 5-positions of the pyrimidine ring, substituents on the 4- and 5-positions of nitro pyrimidine of Formula III must be amine substituents. However, substituents on the 2- and the 6-positions can be a non-amine substituent.

While a wide variety of starting materials and synthetic strategies can be used to produce nitro pyrimidine of Formula III, a tetra-substituted pyrimidine of Formula IV shown below is particularly useful:

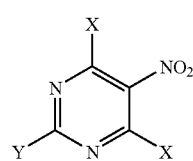

IV where
each X is independently halide; and
Y is $-SO_nR^{10}$, where n is 0, 1, or 2; and $R^{10}$ is alkyl, cycloalkyl, or aryl.

Preferably, each X is independently chloride, fluoride or bromide, more preferably each X is independently chloride or fluoride, and most preferably X is chloride.

Preferably, $R^{10}$ is alkyl, more preferably methyl or ethyl.

The tetra-substituted pyrimidines of Formula IV can be obtained according to a process disclosed by Brown and Jacobsen in *J. Chem. Soc.*, 1965, 3770 and by Harnden and Hurst in *Aust. J. Chem.*, 1990, 43, 55–62, which are incorporated herein by reference in their entirety.

Because of pyrimidine's C-2 symmetry, positions 4- and 6-in pyrimidine of Formula IV are interchangeable. Thus, the order of adding substituents on the 4- and the 6-positions of pyrimidine of Formula IV is not crucial in practicing methods of the present invention. However, for convenience, when a solid-phase synthesis method is used, the first substitution reaction is conducted with a solid-phase having a terminal nucleophile, e.g., secondary amino group, which is used to covalently attach the pyrimidine of Formula IV to the solid support. In this manner, subsequent purification and isolation of product can be conveniently carried out simply by washing the resin with an appropriate solvent to remove any unreacted reagents and/or undesired soluble reaction by-products. A second nucleophilic compound, e.g., a secondary amino compound containing a primary amino group, is then added to afford a nitro pyrimidine of Formula V:

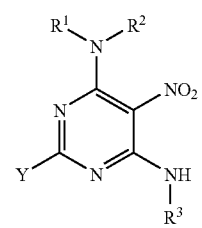

V where $R^1$, $R^2$, $R^3$ and Y are those defined above.

In a solution phase synthesis, it has been discovered by the present inventors that adding about one equivalent of a first amine compound to the nitro pyrimidine of Formula III affords a mono-substituted product almost exclusively, i.e., no statistical mixture of mono- and di-substituted product formation is observed. Without being bound by any theory, it is believed that the reactivity of the nitro pyrimidine ring is significantly reduced by a substitution of one of the halide group with an amino moiety. It is this reduction in reactivity that is believed to be responsible for almost exclusive formation of the non-statistical mixture of a mono-amino substituted nitro pyrimidine compound.

By utilizing this difference in reactivity, one can add both substituents on the 4- and the 6-positions of the pyrimidine ring in a single reaction mixture. In such embodiments, about one equivalent of the first amine compound is added to the nitro pyrimidine compound of Formula III at room temperature to produce a mono-substituted nitro pyrimidine compound. After the reaction is substantially complete, a second amine compound is added to the same reaction mixture to afford a 4,6-diamino substituted pyrimidine compound of Formula V. Typically, the second amine compound is added in excess and the reaction is heated, if necessary, e.g., to at least about 50° C.

Once nitro pyrimidine of Formula V is obtained. The substituent on the 2-position can be added, if desired. For example, when the leaving group Y is a thioether, it is oxidized to a sulfonyl group by reacting the nitro pyrimidine of Formula V with a thioether oxidizing agent. Depending on the nucleophilicity of a third nucleophilic compound that is used to displace the leaving group Y, this oxidation step may or may not be necessary. However, in general oxidation of the thioether affords a sulfonyl group which is a much better leaving group.

The sulfonyl pyrimidine compound is then reacted with a nucleophile, i.e., R⁵—M, to produce a 2, 4, 6-trisubstituted-5-nitro pyrimidine of the formula:

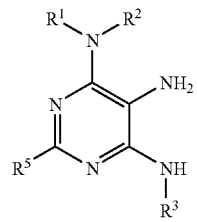

VI

A variety of nucleophiles undergo a substitution reaction with the nitro pyrimidine of Formula V. Exemplary nucleophiles that are capable of displacing the sulfonyl group in the nitro pyrimidine of Formula V include, but are not limited to, alkoxides, aryloxides, enolates, malonates, amines (e.g., where R⁵ is —NR⁸R⁹N), organocuprate compounds (e.g., (R⁵)$_x$Cu, where R⁵ is a conventional group known to one skilled in the art, for example, alkyl, alkenyl, cycloalkyl, and aryl; and x is 1 or 2), organolithium compounds (e.g., R⁵—Li, where R⁵ is a conventional group known to one skilled in the art, for example, alkyl, alkenyl, alkynyl, cycloalkyl, and aryl), Grignard reagents (e.g., R⁵—MgX, where R⁵ is a conventional group known to one skilled in the art, for example, alkyl, alkenyl, cycloalkyl, and aryl; and X is halide), as well as other suitable nucleophiles known to one skilled in the art.

While methods of the present invention are illustrated above in connection with particular reactants and reaction conditions, the present invention is not limited to these reactants and reaction conditions given herein. The reagents and the reaction conditions can vary depending on a particular substituents desired in the purine ring system and to minimize the undesired reaction and/or to increase the yield of the desired product for each reaction.

Some of the compounds described herein may contain one or more asymmetric centers and may thus give rise to enantiomers, diastereomers, geometric isomers, and other stereoisomers which may be defined in terms of absolute stereochemistry as (R) or (S), or as (E) or (Z) for purines comprising an olefin substituent. The scope of present invention includes all such possible isomers as well as their racemic and optically pure forms. Optically active (R) and (S) isomers may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

IV. Combinatorial Library

As described above, the present invention provides methods for producing a highly substituted purine from a pyrimidine compound. Such synthetic methods are useful in producing a single purine compound as well as a combinatorial library of purines. Moreover, methods of the present invention allow a stepwise solution-phase or solid-phase synthesis of the purine ring system. The ability to construct a wide range of substituents on the purine ring allows the construction of libraries having virtually any desired degree of complexity. The possible complexity of the libraries is further enhanced by the stereochemical variations.

In another aspect, the present invention provides a combinatorial library of purines of Formula:

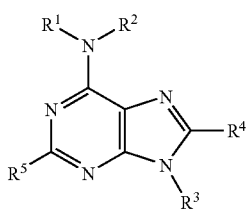

IV

Each compound in the combinatorial library of the present invention comprises a purine structure with various substituents on the 2-, 6-, 8- and the 9-positions of the purine ring system. The substituents are determined by the reagents used in the above-described methods. Some substituents can be in a protected form, which allows further manipulation and derivatization.

A variety of substituents on the purine ring contribute to the structural diversity achievable with this class of compounds, which in turn facilitates the selection of purine compounds with desirable biological activities.

Purine compounds in the combinatorial library are assembled using the methods described above, preferably using a solid phase synthesis method. As described above, methods of the present invention allow selective introduction of various substituents on different purine ring positions. Therefore, a library of purine compounds can be readily prepared by using a mixture of appropriate reagents during any of the steps for introducing a substituent on the purine ring. The resulting substituents should be stable to any subsequent conditions of synthesis and any required protection or deprotection steps, as well as stable under the conditions of use.

A particularly preferred assembly method is a solid phase synthesis in which tetra-substituted pyrimidine of Formula IV is first reacted with a resin to covalently attach the pyrimidine ring structure to a solid support. In this manner, depending on the diversity of the nucleophiles, e.g., amino moieties, bound to the resin, a wide variety of solid support-bound pyrimidines with different substituents on the 6-position can be readily prepared. This solid support-bound pyrimidine is then further elaborated according to methods described herein to produce a library of highly substituted purine compounds. Therefore, hundreds of different purines can be readily prepared using the methods of the present invention.

Combinatorial libraries of the type used in the invention can be formed by a variety of solution phase or solid phase methods in which a homogeneous or a mixture of reagents which form a substituent on the purine ring are added stepwise. Because substituents on each position of the purine ring are added independently, methods of the present invention can be used to prepare a library of purines of known substituent patterns.

Solid-Phase Particle Library

There are many solid phase methods available for preparing a library of compounds. For example, one can simply add a mixture of desired substituents during each step, which results in conducting the synthesis in a single batch. This single batch method allows introduction of a mixture of substituents on any given purine ring position in one reaction. However, if the mixture of reagents comprises compounds of different reactivity, the resulting product may not necessarily contain all the structurally diverse purine compounds as desired.

Alternatively, one can use a split-pool method which avoids problems associated with different reactivity of reagents. In a split-pool method, solid supports, i.e., beads, containing pyrimidines that form the purine library are alternately mixed and separated, with one of a selected number of substituents being added to each group of separated beads at each step. In this manner, each bead in the resulting library contains only one purine specie, allowing a single bead, once identified, as containing the desired purine.

Any conventional size beads (i.e., resins or particles) which are generally used in a solid phase synthesis can be used in the present invention. The bead is preferably derivatized with a linker or a linker functional group, such as by a reductive amination of an aldehyde functional group which is present on the resin. Alternatively, beads can also be covalently attached to a linker which comprises an aldehyde functional group adjacent its distal or free end. Any conventional beads known to one skilled in the art can be modified or derivatized to be useful in methods of the present invention. For example, resins comprising an aldehyde group can be functionalized by reductive amination. Resins comprising an amino group can be used as is or if the amino group is a primary amino group, it can be converted to a secondary amino group or can be mono-protected. Resins comprising a hydroxyl group or a halide group near their surfaces can be modified to afford an amino or an aldehyde functional group on their surface.

Exemplary resins which can be used as a solid support include, but are not limited to, ArgoGel™ resins, such as ArgoGel™-MB-CHO resin, ArgoGel™-Cl resin, ArgoGel™-NH$_2$ resin, ArgoGel™-OH resin, ArgoGel™-Rink-NH-Fmoc resin; ArgoPore™ resins; Merrifield™ resins; and other highly crosslinked macroporous polystyrene resins and commercially available polystyrene resins with amine, hydroxyl, or carboxyl moieties covering their surfaces. These resins can be used directly or can be modified to provide suitable sites for linking suitable tethers or further functionalization.

Linkers or tethers can be any chain of 1 to about 100, preferably 1 to about 50, and more preferably 1 to about 30 atoms where each atom of the chain is independently selected from the group consisting of C, N, O, S, and Si. For example, linkers can be polyethylene glycols and polypropylene glycols.

A linker and/or a tether should be selectively cleavable, stable to conditions used for attaching a various substituents on the purine or pyrimidine ring system, and stable to deprotection conditions for termini and/or substituents. In some instances where the solid phase assay is used to determine activity, the linker should also be stable to the conditions used for assessment of target binding. The linker should also be easily and selectively cleavable under simple conditions.

Resins containing many femtomoles to a few millimoles of functional sites on their surfaces can be used to produce a solid-phase combinatorial library of purines. Portions of the resins can optionally be reacted with a suitable label compound, such as dye, radioactive or fluorescent group, to facilitate identification of substituents present on the purine ring. Alternatively, the label can be incorporated within the particle matrix during the synthesis of the library. Use of labels for identifying the chemical structure within a combinatorial library is well known in the art. See, for example, Still et al., *Complex Combinatorial Chemical Libraries Encoded with Tags*, WO 94/08051, which is incorporated herein by reference in its entirety.

In a typical split-pool method, particles containing at least several times as many particles as there will be purine species in the library are prepared and distributed into equal portions. The number of portions is typically the same as the number of different substituents to be prepared for that particular position of the purine in the library. Each portion of particles is then reacted with a different reagent, e.g., nucleophile or cyclizing compound. After the reaction, all portions of particles are combined, mixed thoroughly, and washed.

Each of the reaction process described above is performed by distributing particles into separate portions. The resulting particles are washed and recombined after each reaction step until the purine ring is formed to give a complete library of purines covalently bound to the particles.

One can also use a parallel synthesis to produce a library of purine compounds. In a parallel synthesis, similar reactions using different reagents are conducted separately in each reaction vessel, e.g., each well of a 96-well reaction apparatus. In this manner, a library of spatially separated purine compounds can be simultaneously synthesized. Since each reaction well comprises a known reagent, the structure of each resulting spatially separated library of purine compound can be readily determined without the need for deconvolution processes. Furthermore, the structure of each purine compound can be determined by its physical properties, such as NMR, IR, UV, MS, melting point, boiling point, x-ray crystallography, etc.

V. Utility

The library of the present invention is useful as a screening tool for discovering new lead structures by evaluation across an array of biological assays, including the discovery of selective kinase inhibitors. The library is thus a tool for drug discovery; i.e., as a means to discover novel lead compounds by screening the library against a variety of biological targets and to develop structure-activity relationships (SAR) in large families of related compounds. The library can be tested with the ligands attached to the solid supports or the purines can be cleaved from the solid support prior to evaluation. When the purine is detached prior to evaluation, its relationship to its solid support can be maintained, for example, by location within the grid of a standard 96-well plate or by location of activity on a lawn of cells. Whether the compounds are tested attached or detached from the solid supports, the tags attached to solid support associated with bioactivity can then be decoded to reveal the structural or synthetic history of the active compound. See, for example, Ohlmeyer et al., *Proc. Natl. Acad. Sci. USA*, 1993, 90, 10922–10926, and Still et al., PCT Publication No. WO 94/08051. Alternatively, the structures can be determined by deconvolution or by their physical characteristics, such as NMR, IR, UV Spectra, mass spectrum, x-ray crystallography, etc. Even if no compounds are found to be active in a given screen, such lack of activity often provides useful SAR information.

Additional objects, advantages, and novel features of this invention will become apparent to those skilled in the art upon examination of the following examples thereof, which are not intended to be limiting.

EXAMPLES
Example 1
This example illustrates a method for synthesizing Olomoucine using the procedure of the present invention.
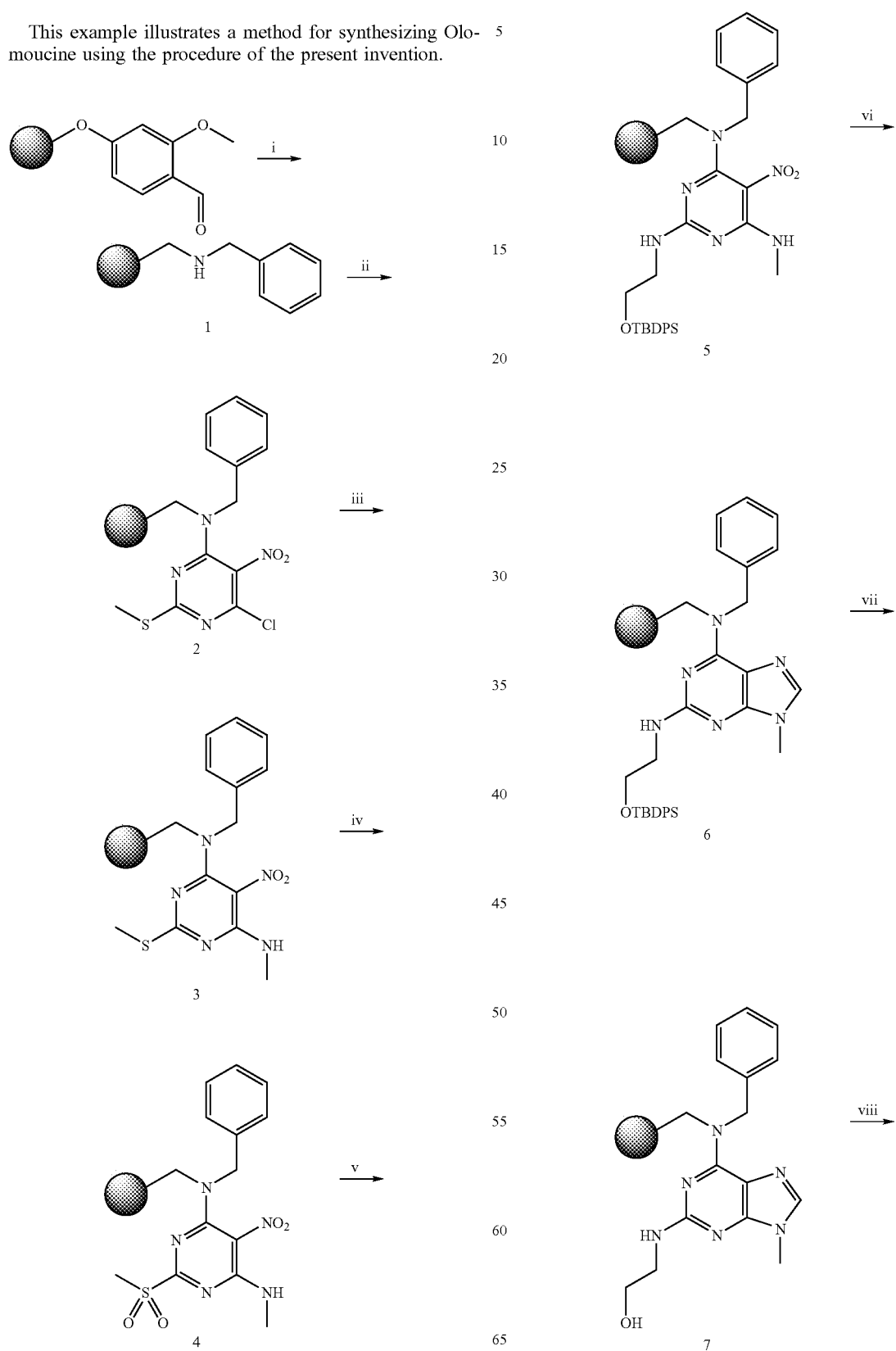

-continued

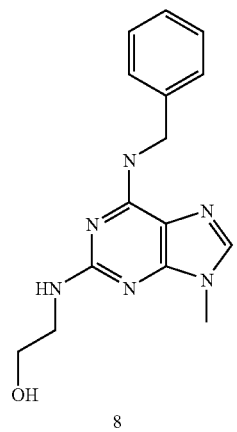

 = ArgoGel

ArgoGel-MB-CHO (0.40 mmol/g substitution) (2.0 g, 0.80 mmol) was suspended in 20 mL of dichloroethane (DCE) and benzyl amine (0.26 g, 2.40 mmol) was added. The reaction was sealed and placed on a rotator for 1 hour. Sodium triacetoxyborohydride (0.51 g, 2.4 mmol), suspended in 5 mL of DCE, was added in one portion to the reaction and the reaction placed on a rotator at room temperature for an additional 24 hours. The resin 1 was then filtered and washed successively with 3 portions of methanol, 3 portions of dichloromethane, 3 portions of methanol and 2 portions of diethyl ether.

The resin 1 (2.0 g, 0.80 mmol) was suspended in 25 mL of tetrahydrofuran and diisopropylethylamine (0.31 g, 2.40 mmol) was added, followed by 4,6-dichloro-2methylmercapto-5-nitropyrimidine (0.58 g, 2.40 mmol). The Reaction was sealed and placed on a rotator for 3 hours at room temperature. The resulting resin 2 was then filtered and washed successively with 3 portions methanol, 3 portions of dichloromethane, 3 portions of methanol and 2 portions of diethyl ether.

The resin 2 (2.0 g, 0.80 mmol) was suspended in 20 mL of nBuOH and methylamine (2.0 M in methanol, 4.0 mL, 8.0 mmol) was added. The reaction was sealed and placed on a rotator for 4 hours at room temperature. The resulting resin 3 was then filtered and washed successively with 3 portions of methanol, 3 portions of dichloromethane, 3 portions of methanol and 2 portions of diethyl ether.

The resin 3 (2.0 g, 0.8 mmol) was suspended in a 25 mL 20:10:1 solution of methanol:dichloromethane:water. Sodium bicarbonate (0.35 g, 4.0 mmol) was added, followed by OXONE® (1.23 g, 2.0 mmol). The reaction was sealed and shaken manually for 15 minutes, venting often. The reaction was then placed on a rotator for 24 hours at room temperature, venting periodically. The resulting resin 4 was then filtered and washed successively with 3 portions of water, 3 portions of methanol, 3 portions of dichloromethane, 3 portions of methanol and 2 portions of diethyl ether.

The resin 4 (2.0 g, 0.8 mmol) was suspended in 25 mL of THF and DIEA (1.03 g, 8.0 mmol) and TBDPS-protected ethanolamine (0.8 g, 2.4 mmol) were added successively. The reaction was placed on a rotator for 24 hours at room temperature. The resulting resin 5 was then filtered and washed successively with 3 portions of methanol, 3 portions of dichloromethane, 3 portions of methanol and 2 portions of diethyl ether.

The resin 5 (2.0 g, 0.8 mmol) was suspended in a 20:1 mixture of DMF:methanol and anhydrous chromium chloride (1.0 g, 8.0 mmol) was added. The reaction was sealed and placed on a rotator for 4 hours at room temperature. The DMF:methanol solution was allowed to drain from the resin and the resin briefly washed with 1 portion of DMF. The resin was then re-suspended in 20 mL of DMF and 5 mL of anhydrous trimethyl orthoformate. Methanesulfonic acid (4 drops) was added to the suspension and the reaction vessel was sealed and shaken at 80° C. for 24 hours. The resulting resin 6 was then cooled to room temperature, filtered and washed successively with 3 portions of methanol, 3 portions of dichloromethane, 3 portions of methanol and 2 portions of diethyl ether.

The resin 6 (2.0 g, 0.8 mmol) was suspended in 20 mL of THF and a 1.0 M TBAF solution in THF (8.0 mL, 8.0 mmol) was added. The resin was placed on a rotator for 2 hours at room temperature. The resulting resin 7 was then filtered and washed successively with 3 portions of methanol, 3 portions of dichloromethane, 3 portions of methanol and 2 portions of diethyl ether.

The resin 7 (2.0 g, 0.8 mmol) was suspended in 20 mL of 95% aqueous trifluoroacetic acid. The reaction vessel was sealed and placed on rotator for 3 hours at room temperature. The resulting resin was filtered and washed successively with 3 portions of dichloromethane, 3 portions of methanol, and 3 portions of water. The filtrate was concentrated in vacuo and diluted with 30 mL of water. The crude was frozen and lyophilized for 48 hours to yield Olomoucine as a fluffy white powder. The resulting crude 8 was stirred with PS-Trisamine resin in dichloromethane for 24 hours, filtered, concentrated and analyzed by LC-MS.

Analytical Data for Olomoucine

Crude: 89% Purity. Purified by flash column chromatography (80:10:1 EtOAc:MeOH:TEA). Yield: 182 mg, purity by LC-MS analysis: 92%. Can be recrystallized to 100% purity from EtOAc-MeOH-Hexane. $^1$H NMR (300 MHz, $d_6$-DMSO) δ 7.82 (br s, 1H), 7.67 (s, 1H), 7.15–7.35 (m, 5H), 6.20 (br s, 1H) (not present in the presence of $D_2O$), 4.63 (m, 2H), 3.54 (s, 3H), 3.48 (m, 2H), 3.31 (m, 2H). $^{13}$C NMR (75 MHz, $d_6$-DMSO) 159.79, 149.9, 141.1, 138.2, 128.4, 127.7, 126.8, 113.6, 60.8, 44.3, 29.2. mp: 129.4–130.3° C. $\lambda_{max}$ 289, 231 ESIMS m/z 299 (M+H)$^+$ Example 2

This example illustrates a method for synthesizing a library of purine compounds on a solid phase.

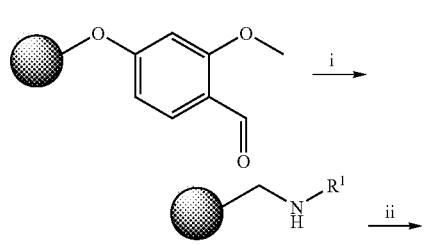

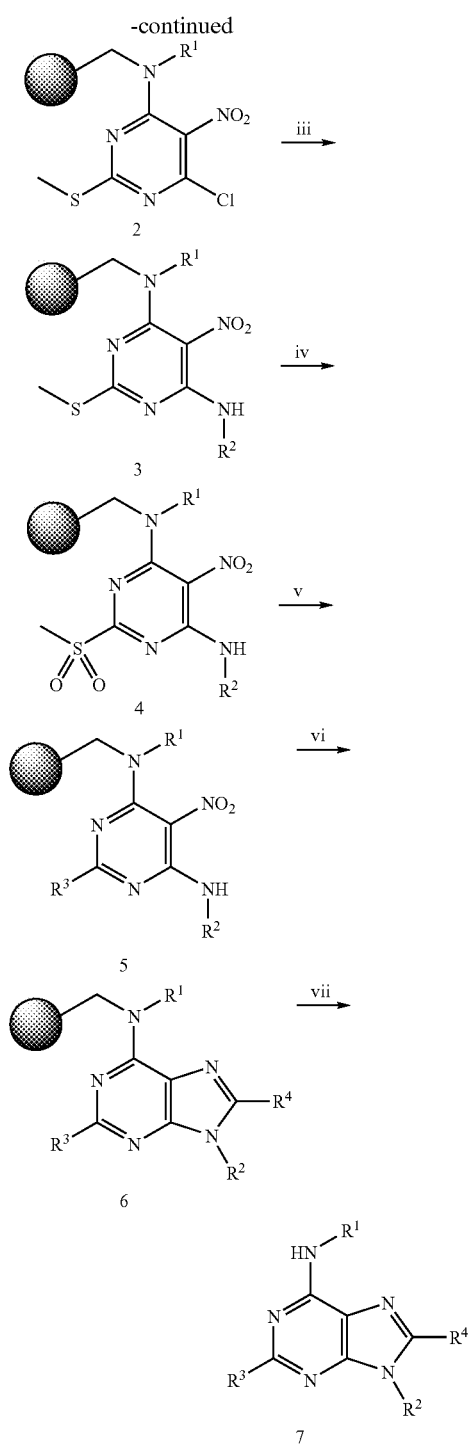

 = ArgoGel

ArgoGel-MB-CHO (0.40 mmol/g substitution) (2.0 g, 0.8 mmol) was suspended in 30 mL of dichloroethane (DCE) and amine $R^1$—$NH_2$ (2.4 mmol) was added. The reaction vessel was sealed and placed on a rotator for 1 hour. Sodium triacetoxyborohydride (0.52 g, 2.4 mmol), suspended in 5 mL of DCE, was added in one portion to the reaction and the reaction placed on a rotator at room temperature for an additional 24 hours. The resin 1 was then filtered and washed successively with 3 portions of methanol, 3 portions of dichloromethane, 3 portions of methanol and 2 portions of diethyl ether.

The resin 1 (2.0 g, 0.8 mmol) was suspended in 30 mL of tetrahydrofuran and diisopropylethylamine (0.31 g, 2.4 mmol) was added, followed by 4,6-dichloro-2methylmercapto-5-nitropyrimidine (0.58 g, 2.4 mmol). The reaction vessel was sealed and placed on a rotator for 3 hours at room temperature. The resulting resin 2 was then filtered and washed successively with 3 portions of methanol, 3 portions of dichloromethane, 3 portions of methanol and 2 portions of diethyl ether.

The resin 2 (2.0 g, 0.8 mmol) was suspended in 30 mL of THF. Diisopropylethylamine (0.31 g, 2.4 mmol) was added, followed by amine $R^2$—$NH_2$ (2.4 mmol). The reaction vessel was sealed and placed on a rotator for 4 hours at room temperature. The resulting resin 3 was then filtered and washed successively with 3 portions of methanol, 3 portions of dichloromethane, 3 portions of methanol and 2 portions of diethyl ether.

The resin 3 (2.0 g, 0.8 mmol) was suspended in a 30 mL 20:10:1 solution of methanol:dichloromethane:water. Sodium bicarbonate (0.34 g, 4.0 mmol) was added, followed by OXONE® (1.23 g, 2.0 mmol). The reaction vessel was sealed and shaken manually for 15 minutes, venting often. The reaction was then placed on a rotator for 24 hours at room temperature, venting periodically. The resulting resin 4 was then filtered and washed successively with 3 portions of water, 3 portions of methanol, 3 portions of dichloromethane, 3 portions of methanol and 2 portions of diethyl ether.

The resin 4 was divided into seven equal portions (0.28 g, 0.12 mmol) and the following manipulations performed on each resin. The resin 4 (0.28 g, 0.12 mmol) was suspended in 10 mL of THF and DIEA (0.05 g, 0.36 mmol) was added, followed by $R^3$—$NH_2$ (0.36 mmol). The reaction mixture was placed on a rotator for 24 hours at room temperature. The resulting resin 5 was then filtered and washed successively with 3 portions of methanol, 3 portions of dichloromethane, 3 portions of methanol and 2 portions of diethyl ether.

The resin 5 (0.28 g, 0.12 mmol) was suspended in a 20:1 mixture of DMF:methanol and anhydrous chromium chloride (0.15 g, 1.2 mmol) was added. The reaction vessel was sealed and placed on a rotator for 4 hours at room temperature. The DMF:methanol solution was removed and the resin was briefly washed with 1 portion of DMF. The resin was then re-suspended in 2:1 DMF:anhydrous orthoester (trimethylorthoformate for $R^4$=H, trimethylorthoacetate for $R^4$=methyl). One drop of methanesulfonic acid was added and the reaction vessel was sealed and shaken at 80° C. for 24 hours. The resulting resin 6 was then cooled to room temperature, filtered and washed successively with 3 portions of methanol, 3 portions of dichloromethane, 3 portions of methanol and 2 portions of diethyl ether.

The resin 6 (0.28 g, 0.12 mmol) was suspended in 5 mL of 95% aqueous trifluoroacetic acid. The reaction vessel was sealed and placed on rotator for 3 hours at room temperature. The resulting resin was filtered and washed with 6 portions of dichloromethane. The filtrate was concentrated in vacuo to yield the crude product. The resulting crude 7 was analyzed by LC-MS (see Table A).

Library Members:
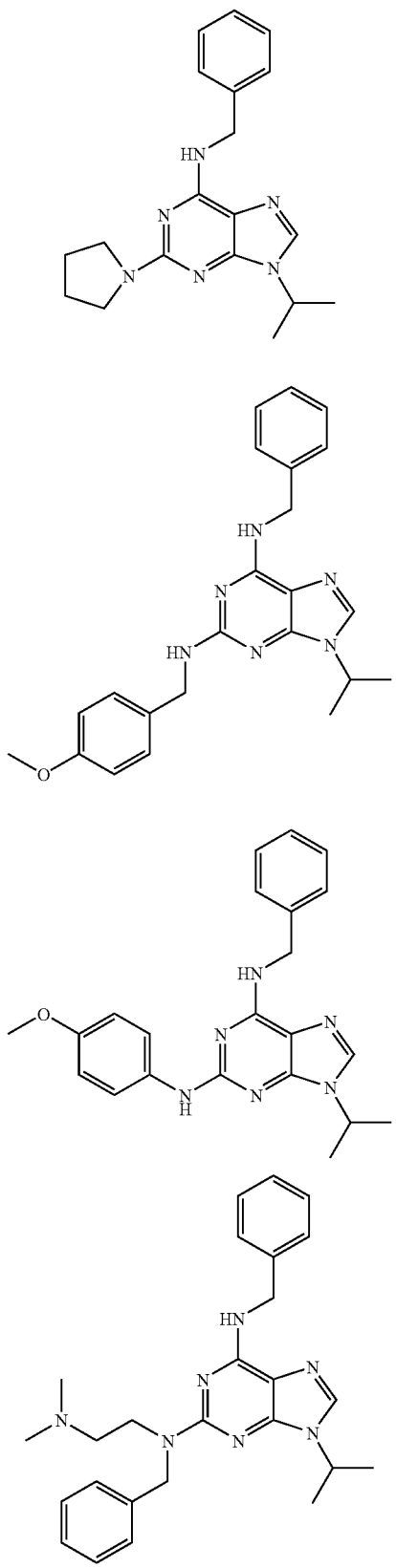
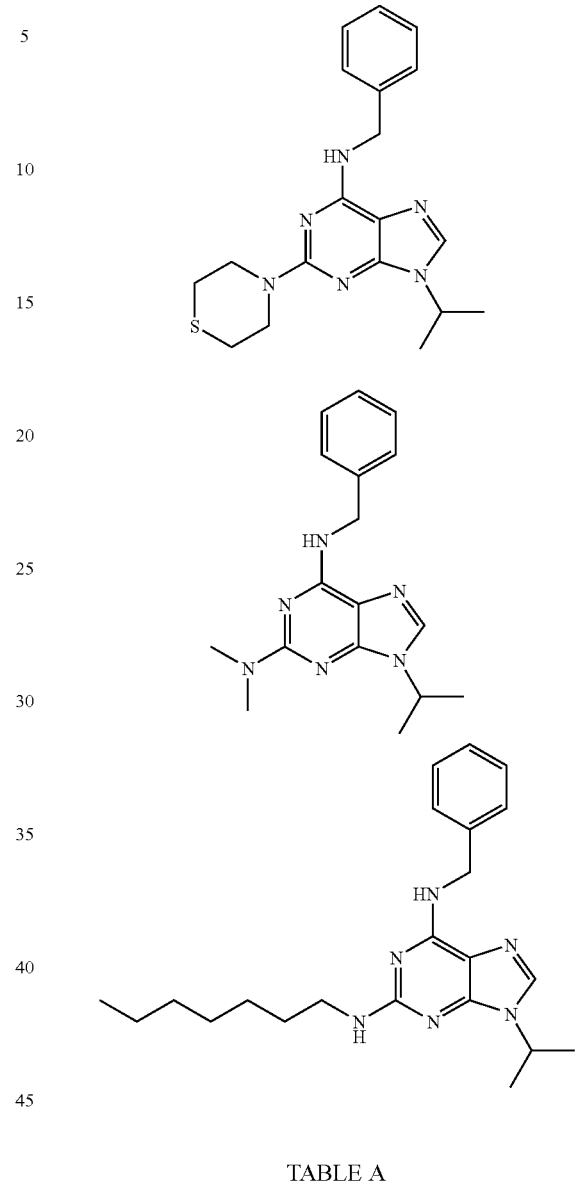
TABLE A
| R1 | R2 | R3 | R4 | LC-MS Purity |
|---|---|---|---|---|
| Benzyl | i-Propyl | Pyrrolidinyl | H | 96.5% |
| Benzyl | i-Propyl | 4-Methoxybenzylamino | H | 50.6% |
| Benzyl | i-Propyl | 4-Methoxyanilinyl | H | 62.4% |
| Benzyl | i-Propyl | N-Benzyl-N-2-(dimethyl-aminoethyl)amino | H | 82.3% |
| Benzyl | i-Propyl | Thiamorpholino | H | 95.2% |
| Benzyl | i-Propyl | Dimethylamino | H | 95.1% |
| Benzyl | i-Propyl | Heptylamino | H | 28.4% |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for producing a substituted purine compound of the formula:

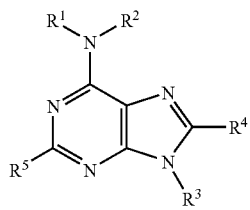

wherein
  $R^1$ is a solid support, hydrogen, alkyl, cycloalkyl, or aryl;
  $R^2$ is alkyl, cycloalkyl, aryl, or a nitrogen protecting group;
  $R^3$ is hydrogen, alkyl, cycloalkyl, aryl, or a nitrogen protecting group;
  $R^4$ is hydrogen, alkyl, aryl, or $NR^6R^7$, where each of $R^6$ and $R^7$ is independently hydrogen, alkyl, aryl, or cycloalkyl; and
  $R^5$ is alkyl, alkoxy, alkenyl, alkynyl, aryl, aryloxy, cycloalkyl, cycloalkoxy, alkylthio, arylthio, or —$NR^8R^9$, where each of $R^8$ and $R^9$ is independently hydrogen, alkyl, cycloalkyl, aryl, or a nitrogen protecting group, or $R^8$ and $R^9$ together with the nitrogen atom to which they are attached to form heterocycle nonaromatic cyclic moiety of 3 to 8 atoms in which one ring atom is a nitrogen and a second ring atom is optionally a $NR^{10}$ (where $R^{10}$ is hydrogen or $C_{1-6}$ alkyl), O or $S(O)_n$ (where n is an integer from 0 to 2), the remaining ring atoms being C, where one or two C atoms may be optionally replaced by a carbonyl group;

said method comprising:
  (a) contacting a 4,6-dihalo-5-nitro-2-thioether pyrimidine of the formula wherein $R^{10}$ is alkyl, cycloalkyl, or aryl and each X is independently halide:

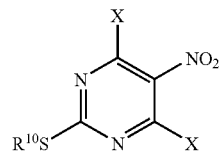

with a first amine compound of the formula $HNR^1R^2$ to produce a 6-aminopyrimidine of the formula:

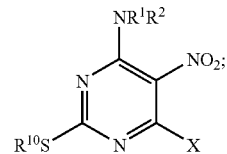

(b) contacting the 6-aminopyrimidine with a second amine compound of the formula $H_2NR^3$ to produce a 4,6-diaminopyrimidine of the formula:

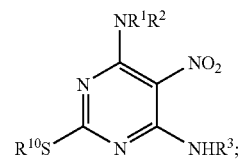

(c) contacting the 4,6-diamino pyrimidine with an oxidizing agent to produce a 2-sulfonylpyrimidine of the formula:

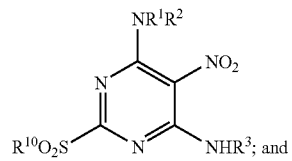

(d) contacting the 2-sulfonylpyrimidine with a nucleophile of the formula $R^5$-M wherein M is hydrogen, alkali metal, copper, or a $R^5$-M is a Grignard reagent, to produce a 5-nitropyrimidine compound of the formula,

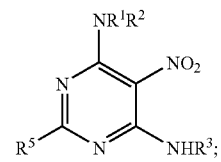

(e) contacting the 5-nitropyrimidine compound with a reducing agent to produce a 4,5,6-triaminopyrimidine of the formula:

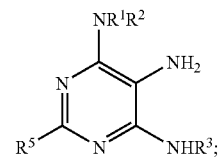

and, (f) forming a purine ring by contacting the 4,5,6-triaminopyrimidine with a cyclizing agent to produce the substituted purine compound.

2. The method of claim 1, wherein $R^1$ is a solid support.

3. The method of claim 2, wherein $R^2$ is a nitrogen protecting group.

4. The method of claim 2, wherein the reducing agent is selected from the group consisting of:

$CrX_2$, wherein each X is independently halide, and a mixture of 1,1'-dialkyl-4,4'-bipyridinium dihalide and a thiosulfate compound.

5. The method of claim 4, wherein the nitro reducing step (a) is done in the presence of a protic solvent.

6. The method of claim 4, wherein the 4,5,6-triaminopyrimidine produced in said step (a) contains less than 10 mole percent of inorganic salts.

7. The method of claim 4, wherein more than 90 mole percent of the solid support-bound pyrimidine ring remains bound to the solid support during said nitro group reducing step (e).

8. The method of claim 2 further comprising cleaving the substituted purine from the solid support to produce the purine compound where $R^1$ is hydrogen.

9. The method of claim 1, wherein the cyclizing agent is an orthoester, a carboxylic acid anhydride, an acyl halide, a mixture of isothiocyanate and an oxidizing agent, a mixture isocyanate and an oxidizing agent, or a mixture of an aldehyde and an oxidizing agent.

* * * * *